United States Patent [19]
Van Wijngaarden et al.

[11] Patent Number: 4,874,770
[45] Date of Patent: Oct. 17, 1989

[54] ARYL-SUBSTITUTED (N-PIPERIDINYL)METHYL- AND (N-PIPERIDINYL) METHYLAZOLES HAVING ANTIPSYCHOTIC PROPERTIES

[75] Inventors: Ineke Van Wijngaarden; Cornelis Kruse; Johannes A. M. Van Der Heyden; Martinus T. M. Tulp, all of Weesp, Netherlands

[73] Assignee: Duphar International Research B.V., Weesp, Netherlands

[21] Appl. No.: 214,310

[22] Filed: Jul. 1, 1988

Related U.S. Application Data

[62] Division of Ser. No. 18,164, Feb. 24, 1987, Pat. No. 4,772,604.

[30] Foreign Application Priority Data

Feb. 27, 1986 [NL] Netherlands ............................ 8600488

[51] Int. Cl.$^4$ .................. A61K 31/445; C07D 211/10; C07D 211/14
[52] U.S. Cl. ..................................... 514/326; 546/208
[58] Field of Search .................. 546/208, 210; 514/326

[56] References Cited

U.S. PATENT DOCUMENTS 4,772,604 9/1988 Van Wijngarden ................ 514/252

OTHER PUBLICATIONS

Yoshitomi Pharm. Ind. Ltd., Chem. Abst. 102-6191j, (1985).
Van Wijngaarden et al., Chem. Abst. 107-217416c, (1987).
Van Wijgaarden et al., Chem. Abst. 108-221717g, (1988).

Primary Examiner—Cecilia Shen
Attorney, Agent, or Firm—Stevens, Davis, Miller & Mosher

[57] ABSTRACT

The invention relates to new aryl-substituted (N-piperidinyl)methyl- and (N-piperazinyl)methylazoles having interesting pharmacological, notably antipsychotic, properties.

The compounds may be prepared in a manner known for the synthesis of analogous compounds and be processed to compositions according to known methods.

4 Claims, No Drawings

ARYL-SUBSTITUTED (N-PIPERIDINYL)METHYL- AND (N-PIPERIDINYL) METHYLAZOLES HAVING ANTIPSYCHOTIC PROPERTIES

This is a division of application Ser. No.018,164 filed Feb. 24, 1987 now patent No. 4,772,604.

The invention relates to new N-(piperidinyl)methyl- and N-(piperazinyl)methylarylazoles having interesting pharmacological, notably antipsychotic, properties, to the preparation of these compounds, and to pharmaceutical compositions comprising at least one of these compounds, a salt, or a derivative thereof as the active substance.

It has been found that compounds of the general formula

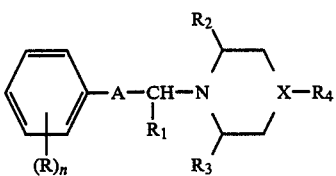

in which the symbols having the following meanings:
R is alkyl, hydroxyalkyl, alkoxy, alkylthio, hydroxy, amino, mono- or dialkylamino, alkyl- or alkoxycarbonyl, nitro, cyano, halogen, trifluoromethyl, trifluoromethoxy, alkyl- or aminosulphonyl;
n is 0-4;
$R_1$, $R_2$ and $R_3$ independently of each other may be hydrogen or alkyl;
X is a nitrogen atom or X is a carbon atom which is substituted with a group $R_5$, in which $R_5$ is hydrogen or hydroxyl, or $R_5$ represents a double bond between carbon atom X and one of the neighbouring carbon atoms;
$R_4$ is aryl or heteroaryl, aryl- or heteroarylcarbonyl optionally substituted with a group $(R)_n$;
A is an unsaturated heterocyclic five-membered ring having 1-3 nitrogen atoms in the ring, with the proviso that the phenyl substitutent is in a meta position with respect to the alkylamino substituent, and that one of the remaining position may be substituted with a group $R_6$, which is alkyl, hydroxyalkyl, halogen or aryl optionally substituted with a group $(R)_n$;
and the acid addition salts and prodrugs thereof have interesting pharmaological, notably antipsychotic, properties.

Compounds which on the basis of their properties are to be preferred are compounds of formula 1, in which
R is alkyl, alkoxy, nitro, cyano, halogen, trifluoromethyl
n is 0-2;
$R_1$, $R_2$ and $R_3$ are hydrogen;
A is a group of formula 2a, 2b or 2c;

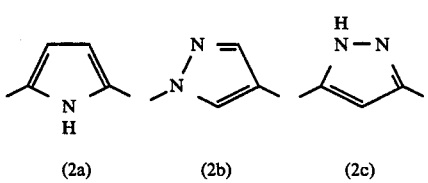

$R_4$ is aryl or aroyl optionally substituted with a group R; mono- or bicyclic heteroaryl or -aroyl of formula 3 optionally substituted with a group R;

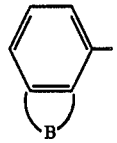

in which B is a saturated or non-saturated chain having a length of 3-5 atoms which comprises at least one oxygen atom, nitrogen atom or sulphur atom, and the remaining symbols have the above-mentioned meanings.

The above-mentioned alkyl groups and hydroxyalkyl groups comprise 1-5 carbon atoms.

Halogen is preferably fluorine, chlorine or bromine;
Optionally present hydroxyl groups may be etherified or esterified.

Compounds according to the invention which are to be preferred in particular are:
(a) 1-[5-(3-chlorophenyl)pyrrol-2-yl] methyl-4-(2-methoxyphenyl)piperazine;
(b) 1-(5-phenylpyrrol-2-yl) methyl-4-(2-methoxyphenyl)piperazine;
(c) 1-[5-(2,6-dichlorophenyl)pyrrol-2-yl] methyl-4-(2-methoxyphenyl)piperazine;
(d) 1-(5-phenylpyrrol-2-yl) methyl-4-(2-methoxy-4-fluorophenyl)piperazine;
(e) 1-[5-(2,6-difluorophenyl)pyrrol-2-yl] methyl-4-(2-methoxyphenyl)piperazine;
(f) 1-[5-(4-fluorophenyl)pyrrol-2-yl] methyl-4-(2-methoxyphenyl)piperazine;
(g) 1-[5-(2-methoxyphenyl)pyrrol-2-yl] methyl-4-(2-methoxyphenyl)piperazine;
(h) 1-[5-(4-fluorophenyl)pyrrol-2-yl] methyl-4-(4-fluorophenyl)piperazine;
(i) 1-[5-(4-fluorophenyl)pyrrol-2-yl] methyl-4-(3-trifluoromethylphenyl)piperazine;
(j) 1-[5-(4-fluorophenyl)pyrrol-2-yl] methyl-2-methyl-4-(2-methoxyphenyl)piperazine;
(k) 1-[5-(4-fluorophenyl)pyrrol-2-yl] methyl-4-(benzo[b]furan-7-yl)piperazine;
(l) 1-(5-phenylpyrrol-2-yl) methyl-4-(2H-3,4-dihydrobenzo-1,5-dioxepin-6-yl)piperazine;
(m) 1-(5-phenylpyrrol-2-yl) methyl-4-[(3-hydroxymethyl)-benzo-1,4-dioxan-5-yl]piperazine;
(n) 2-(5(3)-phenylpyrazol-3(5)-yl) methyl-4-(2-methoxyphenyl)piperazine;
(o) 1-(1-phenylpyrazol-4-yl) methyl-4-(2-methoxyphenyl)piperazine;
(p) 1-(5-phenylpyrrol-2-yl) methyl-4-(2-methoxyphenyl)piperidine;
(q) 1-(5-phenylpyrrol-2-yl) methyl-4-(4-fluorobenzoyl)-piperidine;
(r) 1-[5-(4-fluorophenyl)pyrrol-2-yl] methyl-4-(4-fluorobenzoyl)piperidine;
(s) 1-(1-phenylpyrazol-4-yl)methyl-4-(4-fluorobenzoyl)-piperidine.
(t) 1-(5(3)-phenylpyrazol-3(5)-yl)methyl-4-(4-fluorobenzoyl)piperidine;
(u) 1-[5(3)-(4-fluorophenyl)pyrazol-3-(5)-yl]methyl-4-(2-methoxyphenyl)piperazine.

Examples of suitable acids with which the compounds according to the invention can form pharmaceutically acceptable acid addition salts are hydrocyloric acid, sulphuric acid, phosphoric acid, nitric acid, and organic acids, for example, citric cid, fumaric acid, maleic acid, tartaric acid, acetic acid, benzoic cid, p-tolluenesulphonic acid, methanesulphonic acid, naphthalenesulphonic acid and the like.

Prodrugs are to be understood to mean derivatives of the compounds of formula (1) which as such are inactive and which, after administration into the body, are converted into an active substance of formula 1.

When a chiral centre is present, both the racemate and the individual enantiomers fall within the scope of this invention.

The compounds according to the invention have interesting psychotropic properties and are consequently suitable for the treatmment of affections and diseases which are the result of disturbances in the central nervous system. The compounds notably have a specific antipsychotic activity.

The antipsychotic activity was determined in a test procedure in which the suppression of conditioned behaviour in experimental animals (rats) was measured in a manner known per se. The compounds are qualified as active when in this test they show at least 50% suppression of the conditioned behaviour after oral administration of 100 mg per kg of body weight or less.

For the greater part of the compounds of formula (1) according to the invention it holds that the cataleptic properties found in nuroleptics are not found or are found to a considerably smaller extent. This cataleptic effect was determined in a test in which it was established in rats how long they accepted an unnatural posture, for example, a standing posture with both front legs supported on a noted rod. It was found that no extension of the time in the unnatural posture ocurred in the behaviour test with doses which are at least 10 times higher than the active dose.

The dopaminolytic properties of the compounds were determined in mice by means of a test procedure in which the extent of inhibition of behaviour (climbing behaviour) was established which is induced by the dopamine agonist apomorphine. A compound is considered to be active when after oral administration of doses smaller than 50 mg/kg an inhibition of more than 50% is found.

In addition to the above-described in vivo tests, in vitro receptor-binding tests were also carried out by means of radioactive-labelled ligand in brain tissue homogenates. The preferred compounds show a pronounced selectivity for dopamine D-2 receptors with binding affinities (expressed in $K_i$-values) less than 10 nM.

The combination of the results of these in vivo and in vitro tests indicate that these compounds could have an interesting clinical profile, in the sence that the antipsychotic activity is not associated with the occurrence of so-called extrapyrimidal side-effects which are characteristic for all classical neuroleptics used so far in the clinic.

The quantity, frequency, and mode of administration may differ for each individual case, also dependent on the nature and the severity of the disturbances. In general, a dose of 5–500 mg daily, and preferably 5–100 mg daily, preferably in one dose daily, may be used for humane applications.

The active compounds according to the invention and their salts and prodrug forms can be processed by means of standard methods known per se to compositions such as pills, tablets, coated tablets, capsules, powders, injection liquids, and the like, while using the conventional auxiliary substances such as solid and liquid carrier materials.

The compounds and their acid addition salts, prodrugs and enantiomers, may be brought into a form suitable for administration in a manner known per se.

The new compounds according to the invention can be prepared according to methods known for the synthesis of analogous compounds, for example, as described in Belgian Patent Specification 853899.

Suitable methods for the preparation of the compounds of formula 1 as a rule comprise the reaction of a secondary amine of formula 4 with a suitable reagent which comprises the structural fragment of formula 5:

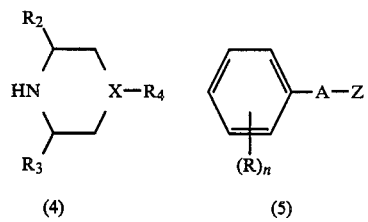

The compounds of formula 1 in which A is a group of formula 2a can be obtained in the above manner, for example, by means of a so-called Mannich reaction. In this reaction the adduct which is formed after treating a compound of formula 4 with formaldehyde, is converted with a 2-phenylpyrrol derivative, i.e. a compound of formula 5 in which Z is hydrogen. This reaction is carried out in an organic solvent, preferably a protic solvent, and may be accelerated, if desired, by the addition of an organic or inorganic acid as a catalyst. The reaction temperature is preferably between room temperature and the boiling-point of the solvent used.

The starting substances of formula 4 in wich $R_4$ is the group of formula 3, are partly known from Netherlands Patent Application 8303569 and, in so far as they are new, they can be obtained in an analogous manner.

The 2-phenylpyrroles of formula 5 to be used in this mode of preparation can be obtained by cyclisation of the corresponding 1,4-dicarbonyl compounds (Monatshefte für Chemie 108, (1977), p. 285).

Compounds of formula 1 in which A is a group of formula 2b or 2c can be obtained by alkylating a compound of formula 4 with a reactive compound of formula 5 in which Z is the group —CH$_2$—Y and Y is a so-called "leaving" group, preferably chlorine, bromine, aryl- or alkylsulphonyl, etc. This reaction may be carried out under mild conditions in an organic solvent. The formed acid is preferably neutralized by means of an inorganic base. For example, K$_2$CO$_3$, or an organic base, for example, triethylamine. Suitable solvents are, for example, tetrahydrofuran, acetonitrile, dimethyl formamide, toluene and dioxane. The reaction temperature may vary between 0° C. and the reflux temperature of the solvent used.

The reactive starting compounds 5 in which Z is the group —CH$_2$—Y can be obtained in known manner, as described in J. Chem. Soc. (1954), p. 2293, and J. Org. Chem. 19 (1954), pp. 1428 and 1431.

A suitable mode of preparing compounds of formula 1 in which $R_1$ is an alkyl group, is the reaction of a compound 4 with a compound 5 in which Z is the group —C(R$_1$)=O, under the influence of a mild reducing agent, for example, sodium cyanoborohydride. It is also possible first to introduce the group Z at the nitrogen atom of compound 4 and to activate the amide thus formed with a strong Lewis acid, for example, phosphoroxytrichloride, and then to convert it with a compound of formula 5, in which Z is hydrogen.

Another method of preparing compounds of formula 1 in which $R_1$ is hydrogen, comprises the reduction of the tertiary amide which is obtained after reaction of a compound 4 with a compound 5 in which Z is a group —C(Y')=O, in which Y' may have the same meaning as Y or is an alkoxy group. Suitable reduction agents for this reduction reaction which is preferably carried out in ether, tetrahydrofuran or toluene, are notably lithium aluminum hydride and borohydride.

When in formula 1 the groups R, $R_5$ and/or $R_6$ are or comprise a hydroxyl group, such compounds can also be obtained by splitting off a protective group from corresponding compounds of formula 1 as the last reaction step. Other chemical conversions within the meanings of R and $R_1$-$R_6$, for example, reduction reactions, may be used as the last reaction step to prepare compounds of formula 1.

The invention will now be described in greater detail with reference to the ensuing specific examples.

EXAMPLE I

2-Aryl-5-(N-piperazinyl)methylpyrroles and 2-aryl-5-(N-piperidinyl)methylpyrroles.

1.2 Ml of formalin (37% formaldehyde in water) were added to a solution of 15 mMol of secondary amine of formula 4 in 75 ml of ethanol. The mixture was stirred at 20° C. for 30 minutes and, after the addition of 15 mMol of 2-arylpyrrole it was stirred at reflux temperature for 4 hours. After evaporating the solvent, the mixture was chromatographed over silica gel with methylene chloride-methanol (5-10 vol. %) mixtures. Piperazines 1-19 and piperidines 20-30 as stated in tables A and B hereinafter were obtained after evaporating the fractions which comprise the pure products in yields of 40-70%. A number of compounds were converted in the HCl salt by treating with 1 equivalent of a HCl solution in ethyl acetate. According to another method, first 1 equivalent of acetic acid and sodium acetate, respectively, were added to the solution of the amine of formula 4 as the free base and the HCl salt, respectively. The coupling reaction with the 2-arylpyrrole in this catalyzed process was completed after stirring for 2-18 hours at 20° C.

TABLE A

2-Aryl-5-(N—piperazinyl)methylpyrroles

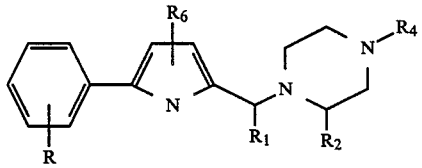

| Comp. no. | R | $R_1$ | $R_2$ | $R_4$ | $R_6$ | salt | melt. point °C. |
|---|---|---|---|---|---|---|---|
| 1 | H | H | H | 4-fluorophenyl | H | base | 140-142 |
| 2 | H | H | H | 2-methoxyphenyl | H | base | 125-127 |
| 3 | 4-fluoro | H | H | 2-methoxyphenyl | H | base | 118-120 |
| 4 | H | H | H | 2-methoxy-4-fluorophenyl | H | HCl | 140-142 |
| 5 | H | methyl | H | 2-methoxyphenyl | H | base | 134-136 |
| 6 | 4-fluoro | H | H | 4-fluorophenyl | H | base | oil |
| 7 | 4-fluoro | H | H | 3-trifluoromethylphenyl | H | base | oil |
| 8 | 2-methoxy | H | H | 2-methoxyphenyl | H | base | 107-108 |
| 9 | 3-chloro | H | H | 2-methoxyphenyl | H | base | 117-119 |
| 10 | 4-fluoro | H | H | 7-benzo[b]furanyl | H | base | 118-119 |
| 11 | 2,6-difluoro | H | H | 2-methoxyphenyl | H | base | oil |
| 12 | H | H | H | 8-(2-hydroxymethyl-1,4-benzodioxanyl) | H | base | 90-93 |
| 13 | 2,6-dichloro | H | H | 2-methoxyphenyl | H | base | oil |
| 14 | H | H | H | 6-(1,5-benzo[b]-1,5-dioxepanyl) | H | HCl | 142-146 |
| 15 | 4-trifluoromethyl | H | H | 2-methoxyphenyl | H | base | 55-60 |
| 16 | 4-isopropyl | H | H | 2-methoxyphenyl | H | base | 129-131 |
| 17 | 4-fluoro | H | methyl | 2-methoxyphenyl | H | base | 56 |
| 18 | 4-fluoro | H | H | 4-fluorobenzoyl | H | base | 121-122 |
| 19 | H | H | H | 2-methoxyphenyl | 3-phenyl | base | 112-113 |
| 20 | 2-methoxy-5-sulfonylethyl | H | H | 2-methoxyphenyl | H | 0.25 acetic acid | 122-124 |
| 21 | 2-methoxy-3,5-dibromo | H | H | 2-methoxyphenyl | H | base | 70 (decom.) |
| 22 | 4-fluoro | H | H | 2-methoxyphenyl | 1-$CH_3$ | base | 111-113 (decom.) |

TABLE B

2-Aryl-5-(N—piperidinyl)methylpyrroles

| Comp. no. | R | R4 | R5 | salt | melt. point °C. |
|---|---|---|---|---|---|
| 23 | H | 4-fluorobenzoyl | H | base | 128–130 |
| 24 | 4-fluoro | 4-fluorobenzoyl | H | base | 135–139 |
| 25 | 3-chloro | 4-fluorobenzoyl | H | HCl | 181–183 |
| 26 | 2-methoxy | 4-fluorobenzoyl | H | HCl | 141–143 |
| 27 | 2,6-difluoro | 4-fluorobenzoyl | H | base | 78–81 |
| 28 | 4-fluoro | phenyl | H | base | 102–103 |
| 29 | H | 2-methoxyphenyl | H | HCl | 120–125 |
| 30 | H | 4-chlorophenyl | OH | base | 84–86 |
| 31 | 4-fluoro | 4-chlorophenyl | OH | base | 125–127 |

EXAMPLE II 1-(1-phenylpyrazol-4-yl)methyl-4-(2-methoxyphenyl)-piperazine.

5 mMol (0.96 g) of 1-(2-methoxyphenyl)piperazine together with 5 mMol (0.97 g) of 1-phenyl-4-chloromethyl)pyrazole and 5.3 mMol (0.75 ml) of triethylamine were dissolved in 10 ml of dry acetonitrile. The mixture was heated at reflux temperature while stirring for 2 hours under an atmosphere of nitrogen. The reaction mixture was then evaporated and divided over a basic aqueous layer and an ethyl acetate layer. After the extraction procedure, drying and evaporating the organic layer, the crude product was obtained. Crystallization from a mixture of ethyl acetate and cyclohexane yielded 0.74 g of the desired product having a melting-point of 121°–125° C.

The compounds indicated in table C below were prepared in a similar manner:

EXAMPLE III 1-(5(3)-phenylpyrazol-3(5)-yl)methyl-4-(2-methoxyphenyl)piperazine.

In a manner analogous to Example II, 10 mMol (1.92 g) of 1-(2-methoxyphenyl)piperazine were reacted with 10 mMol (2.29 g) of 3(5)-(chloromethyl)-5(3)-phenylpyrazole. After the extraction procedure the reaction mixture was chromatographed over silica gel using a mixture of chloroform, methanol and ammonia in the ratio 90:10:1 as an eluent, which after evaporating the pure fractions yielded 1.25 g of product having a melting-point of 136°–138° C.

The compounds listed in Table D have been prepared in a similar manner.

TABLE D

A

B

| Comp. no. | Formula | R | R4 | R5 | Salt | Melt. point (°C.) |
|---|---|---|---|---|---|---|
| 40 | A | 4-F | 2-methoxyphenyl | — | HCl | 190 (decom.) |
| 41 | A | 4-Cl | 2-methoxyphenyl | — | NaOH | 147–1492 (decom.) |
| 42 | A | H | 7-benzo[b]furanyl | — | fumarate | oil |
| 43 | A | 4-F | 7-benzo[b]furanyl | — | base | 142–143 |
| 44 | B | — | 4-fluorobenzoyl | H | base | 161–164 |

We claim:
1. Compounds of formula 1

TABLE C

A

B

| Comp. no. | Formula | R | R4 | R5 | Salt | Melt. point (°C.) |
|---|---|---|---|---|---|---|
| 32 | A | H | 4-fluorophenyl | — | base | 112–113 |
| 33 | A | 2-Cl | 2-methoxyphenyl | — | 2HCl | 211.5–212.5 |
| 34 | A | 3-Cl | 2-methoxyphenyl | — | base | 123–124 |
| 35 | A | 4-F | 2-methoxyphenyl | — | base | 118 |
| 36 | A | 4-HO2 | 2-methoxyphenyl | — | base | 148–149 |
| 37 | B | — | 2-methoxyphenyl | H | HCl | 99–100 |
| 38 | B | — | 4-fluorobenzoyl | H | base | 118–120 |
| 39 | B | — | 4-chlorophenyl | OH | HCl | 233–234 |

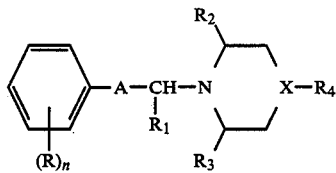 (1)

in which the symbols have the following meanings:
R is methyl, methoxy or halogen;
n is 0-2;
$R_1$, $R_2$ and $R_3$ are hydrogen;
X is a carbon atom which is substituted with a group $R_5$, in which $R_5$ is hydrogen or hydroxyl;
$R_4$ is phenyl or benzoyl, which may be substituted with halogen or methoxy;
A is pyrrole or pyrazole, which may be substituted with methyl or phenyl; and the acid addition salts and prodrugs thereof.

2. Compounds as claimed in claim 1:
(r) 1-[5-(4-fluorophenyl)pyrrol-2-yl] methyl-4-(4-fluorobenzoyl)piperidine;
(s) 1-(1-phenylpyrazol-4-yl)methyl-4-(4-fluorobenzoyl)piperidine; and
(t) 1-(5(3)-phenylpyrazol-3-(5)-yl)methyl-4-(4-fluorobenzolyl)piperidine.

3. Pharmaceutical compositions which comprise at least an effective amount of one compound as claimed in claim 1 as the active substance.

4. A method of treating affections in the central nervous system, characterized in that an effective amount of a compound as claimed in claim 1 is used.

* * * * *